(12) United States Patent
Montaser et al.

(10) Patent No.: US 7,317,186 B2
(45) Date of Patent: Jan. 8, 2008

(54) SHORT TORCH DESIGN FOR DIRECT LIQUID SAMPLE INTRODUCTION USING CONVENTIONAL AND MICRO-NEBULIZERS FOR PLASMA SPECTROMETRY

(75) Inventors: Akbar Montaser, Potomac, MD (US); Craig S. Westphal, Landenberg, PA (US); Kaveh Kahen, Montgomery Village, MD (US); William F. Rutkowski, Arlington, VA (US)

(73) Assignee: The George Washington University, Washington, DC (US)

( * ) Notice: Subject to any disclaimer, the term of this patent is extended or adjusted under 35 U.S.C. 154(b) by 364 days.

(21) Appl. No.: 11/018,919

(22) Filed: Dec. 22, 2004

(65) Prior Publication Data

US 2005/0224709 A1 Oct. 13, 2005

Related U.S. Application Data

(60) Provisional application No. 60/534,194, filed on Jan. 2, 2004, provisional application No. 60/531,610, filed on Dec. 23, 2003.

(51) Int. Cl.
 *F23D 14/62* (2006.01)

(52) U.S. Cl. .................... 250/288; 250/281; 250/282; 250/285; 250/286; 250/292; 356/316; 356/16

(58) Field of Classification Search ............... None
See application file for complete search history.

(56) References Cited

U.S. PATENT DOCUMENTS

| | | | |
|---|---|---|---|
| 3,550,858 A | 12/1970 | Larrabee et al. | |
| 3,552,657 A | 1/1971 | Chisholm et al. | |
| 4,125,225 A | 11/1978 | Venghiattis | |
| 4,517,495 A | 5/1985 | Piepmeier | |
| 4,575,609 A * | 3/1986 | Fassel et al. | 219/121.59 |
| 4,990,740 A | 2/1991 | Meyer | |
| 5,066,125 A | 11/1991 | Rogers | |
| 5,400,665 A * | 3/1995 | Zhu et al. | 73/863.12 |
| 5,884,846 A | 3/1999 | Tan | |
| 6,126,086 A | 10/2000 | Browner et al. | |
| 6,166,379 A | 12/2000 | Montaser et al. | |
| 6,729,334 B1 | 5/2004 | Baran | |
| 7,005,635 B2 * | 2/2006 | Ahern et al. | 250/288 |

OTHER PUBLICATIONS

A. Montaser; "Inductively Coupled Plasma Mass Spectrometry"; Wiley-VCH, New York, 1998.

(Continued)

*Primary Examiner*—Jack I. Berman
*Assistant Examiner*—Zia Hashmi
(74) *Attorney, Agent, or Firm*—Roylance, Abrams, Berdo & Goodman, L.L.P.

(57) ABSTRACT

An apparatus and method for providing direct liquid sample introduction using a nebulizer are provided. The apparatus and method include a short torch having an inner tube and an outer tube, and an elongated adapter having a cavity for receiving the nebulizer and positioning a nozzle tip of the nebulizer a predetermined distance from a tip of the outer tube of the short torch. The predetermined distance is preferably about 2-5 mm.

20 Claims, 7 Drawing Sheets

OTHER PUBLICATIONS

J.A. McLean, H. Zhang, and A. Montaser; "A Direct Injection High Efficiency Nebulizer for Inductively Coupled Plasma Mass Spectrometry"; Anal. Chem 70; 1012-1020; 1998.

J.-L Todoli and J.-M. Mermet; "New Torch Design With and In-Built Chamber For Liquid Sample Analysis"; ICP-AES; J. Anal. At. Spectrom. 17, 345-351 (2002).

Craig S. Westphal, K. Kahen, W.F. Rutkowski, B.W. Acon, and A. Montaser; "Demountable Direct Injection High Efficiency Nebulizer for Inductively Coupled Plasma Mass Spectrometry"; Spectrochimica Acta Part B 59, 353-368 (2004).

J.-L. Todoli and J.-M. Mermet; Optimization of the Evaporation Cavity in a Torch Integrated Sample Introduction System Based ICP-AES System. Applications to Matrix and Transient Effects, Analysis of Microsamples and Analysis of Certified Solid Samples: J. Anal. At Spectrom. 18, 1185-1191 (2003).

* cited by examiner

SHORT TORCH DESIGN FOR DIRECT LIQUID SAMPLE INTRODUCTION USING CONVENTIONAL AND MICRO-NEBULIZERS FOR PLASMA SPECTROMETRY

PRIORITY

The present application claims priority from U.S. Provisional Patent Application Ser. No. 60/531,610, entitled "Short Torch Design For Direct Liquid Sample Introduction Using Conventional And Micro-Nebulizers For Plasma Spectrometry", filed on Dec. 23, 2003, and U.S. Provisional Patent Application Ser. No. 60/534,194, entitled "Short Torch Design For Direct Liquid Sample Introduction Using Conventional And Micro-Nebulizers For Plasma Spectrometry", filed on Jan. 2, 2004, the entire contents of both of said applications being incorporated herein by reference.

This application was made with United States Government support under Grant No. DE-FG02-93ER14320 awarded by the U.S. Department of Energy. The U.S. Government has certain rights in the invention.

CROSS REFERENCE TO RELATED PATENT AND APPLICATION

Related subject matter is disclosed in U.S. Pat. No. 6,166,379, entitled "Direct Injection High Efficiency Nebulizer For Analytical Spectrometry", issued on Dec. 26, 2000 to Akbar Montaser et al., and a U.S. Nonprovisional Patent Application having filed concurrently herewith, entitled "Demountable Direct Injection High Efficiency Nebulizer For Inductively Coupled Plasma Mass Spectrometry", the entire contents of said patent and application being incorporated herein by reference.

BACKGROUND OF THE INVENTION

1. Field of the Invention

This application relates generally to nebulizers for use in analytical spectrometry such as inductively coupled mass spectrometry, and more specifically to conventional pneumatic nebulizers suitable for short torch design.

2. Description of the Related Art

Inductively coupled plasma atomic emission spectrometry (ICPAES) and ICP mass spectrometry (ICPMS) are practical techniques for trace and ultratrace elemental analysis. While many advances have been made in instrumentation, the introduction of a sample to the plasma represents the most problematic area, with liquid sample introduction being the most common. Many devices have been developed for aerosol generation and transport, each having its own benefits and limitations.

The pneumatic nebulizer-spray chamber arrangement is currently the primary sample introduction method for ICP spectrometry, mainly due to its simplicity and low cost. This arrangement presents, however, several drawbacks, namely low analyte transport efficiency (1-20%) and high sample consumption (1-2 mL/min), memory effects, spray chamber-induced interferences such as transient acid effects, and post-column broadening when coupled with chromatographic techniques for speciation analysis. These effects may be reduced through the use of micronebulizers and reduced-volume spray chambers integrated with or without the ICP torch. A simple, low-consumption, highly efficient nebulizer is often required in chromatographic applications and also for the direct analysis of semiconductor, biological, toxic, or forensic materials. In these and other cases, the sample is expensive, hazardous, or limited.

Two popular micronebulizers have been explored that eliminate the need for the spray chamber by directly introducing 100% of the sample into the plasma: the direct injection nebulizer (DIN) and the direct injection high efficiency nebulizer (DIHEN). Both devices offer fast response times, reduced memory effects, no transient acid effects, no solution waste and low sample consumption rates (1-100 µL/min) while exhibiting similar or improved detection limits, sensitivity and precision compared to conventional nebulizer-spray chamber arrangements. The versality of the DIN is limited due to its relatively complex setup, high costs, and requirement of a high-pressure pump for sample delivery. The DIHEN, however, is a simple concentric nebulizer that is less expensive compared to the DIN and does not require an additional high-pressure pump.

One weakness of the micronebulizers (including the DIN and DIHEN) in addition to their high cost (for example, direct injection nebulizers can cost 10 to 100 times as much as conventional nebulizers), is their greater susceptibility to nebulizer clogging compared to other types of nebulizers due to the smaller dimensions for the solution capillary and gas annulus areas. This limitation may destroy the nebulizer. In order to overcome the problem of clogging a large bore-DIHEN (LB-DIHEN) is used. Although nebulizer clogging is reduced for nebulization of slurries and solutions having a large amount of total dissolved solids, the performance of the LB-DIHEN is slightly worse than those of the DIHEN. Additionally, the close proximity of the nebulizer tip to the plasma increases the likelihood of accidental and gradual damage to direct injection nebulizers.

Therefore an apparatus is needed that can provide significantly improved analytical performance by directly introducing 100% of the analyte into the plasma without incurring undue cost and damage to the nebulizer. In addition, the apparatus should operate with conventional nebulizers allowing the nebulizers to be more efficient.

SUMMARY OF THE INVENTION

A new torch apparatus and method are provided in accordance with an embodiment of the present invention to facilitate the direct injection of liquid samples into plasma using conventional and micro-pneumatic nebulizers.

According to an aspect of the present invention, an apparatus and method for providing direct liquid sample introduction using a nebulizer are provided. The apparatus and method include a short torch having an inner tube and an outer tube, and an elongated adapter having a cavity for receiving the nebulizer and positioning a nozzle tip of the nebulizer a predetermined distance from a tip of the outer tube of the short torch.

The predetermined distance between the tip of the nozzle and the end of the intermediate tube is preferably between 2-5 mm, and the elongated adapter preferably comprises a high temperature resistant material.

BRIEF DESCRIPTION OF THE DRAWINGS

These and other objects, advantages and novel features of the invention will be more readily appreciated from the following detailed description when read in conjunction with the accompanying drawings, in which.

DETAILED DESCRIPTION OF THE PREFERRED EMBODIMENT

Figure 1:
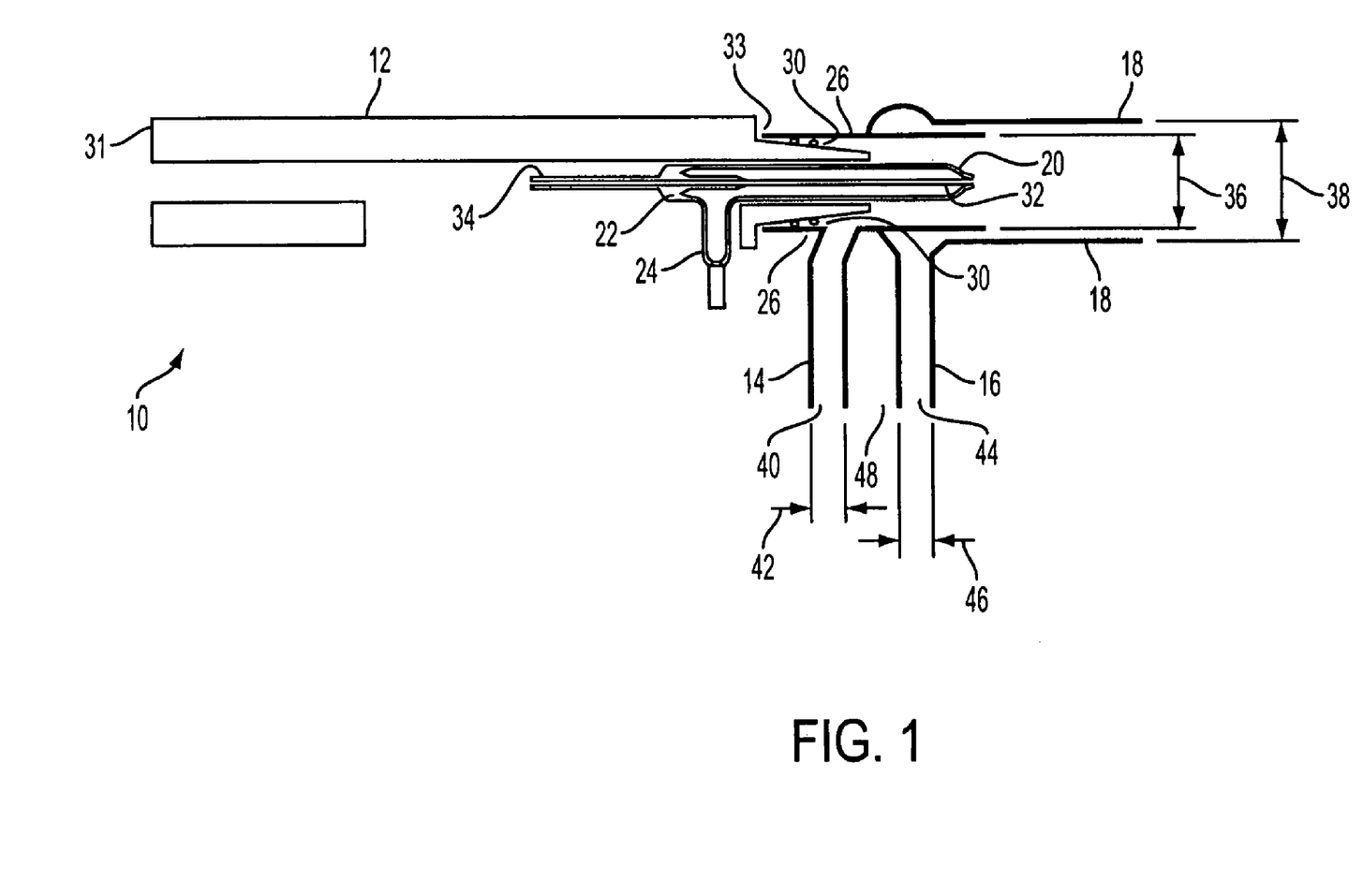
FIG. 1 is a diagram of a short torch with an adapter and high efficiency nebulizer (HEN) in accordance with an embodiment of the present invention.
Figure 2:
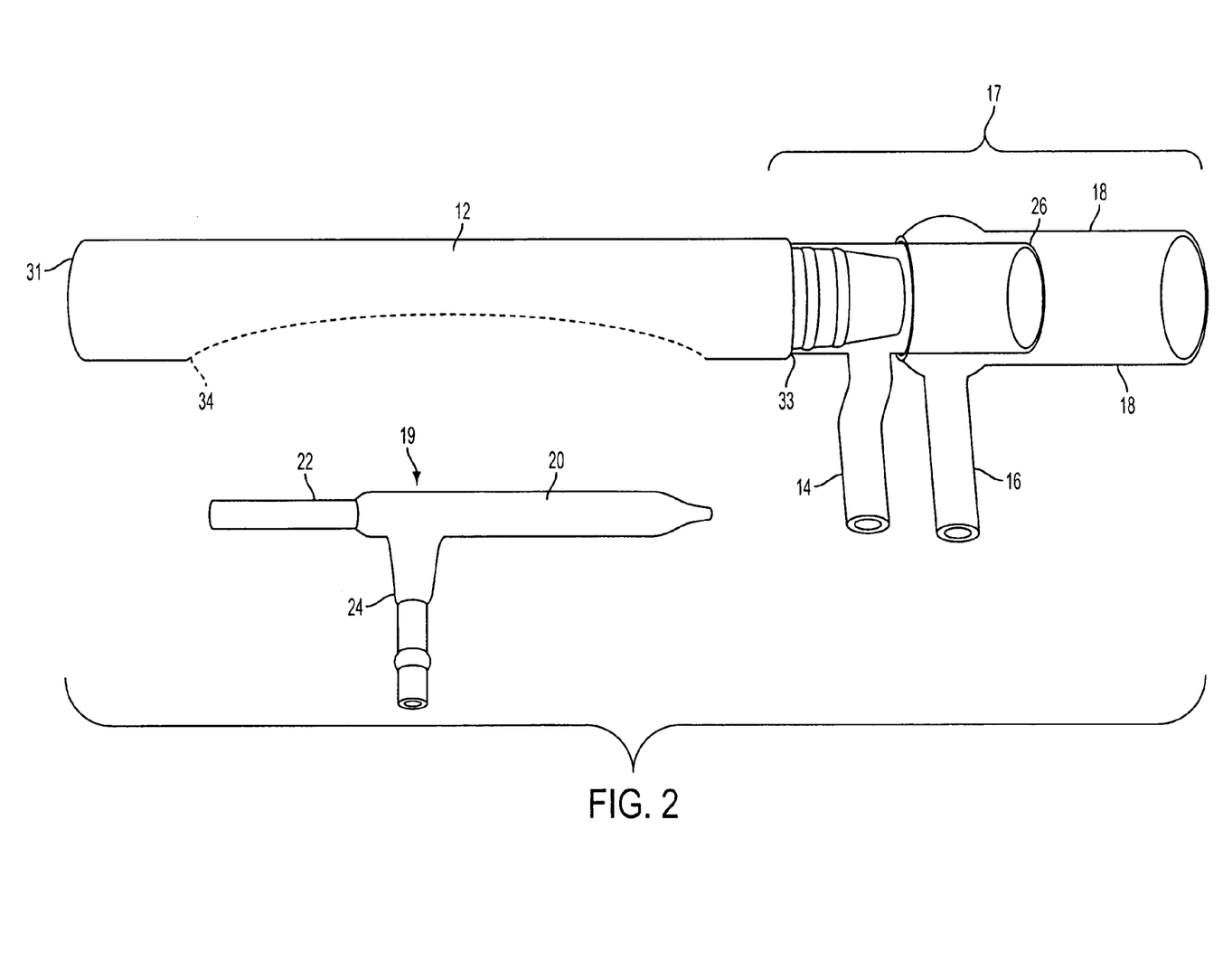
FIG. 2 is a diagram of the short torch with a detached adapter and HEN in accordance with an embodiment of the present invention.

A schematic diagram of an exemplary short torch design 10 includes a torch 17 and adapter 12. The short torch design 10 operates with any conventional nebulizer. The nebulizer shown in FIG. 2 is a high efficiency nebulizer (HEN) 19. The HEN 19 is a conventional HEN having a nozzle 20, a solution connector 22 for receiving a solution, and a gas inlet 24. The HEN 19 may also include a capillary 32. It should be appreciated by those skilled in the art that embodiments of the present invention are adaptable to operate with any type of nebulizer. The tables and graphs, which will be described later, compare the operation of different types of nebulizers with and without the use of the short torch design 10.

The adapter 12 comprises a high temperature resistant material, for example, Delrin. However, it should be appreciated by those skilled in the art that any high temperature resistant material can be substituted without departing from the scope of the present invention. The adapter 12 is elongated and tubular in design having an elongated cavity 34, a closed end 31, and a tapered open first end 30 leading from a neck 33 of the adapter 12. The elongated cavity 34 is structured and arranged to accept any type of nebulizer such as HEN 19.

Figure 3A:
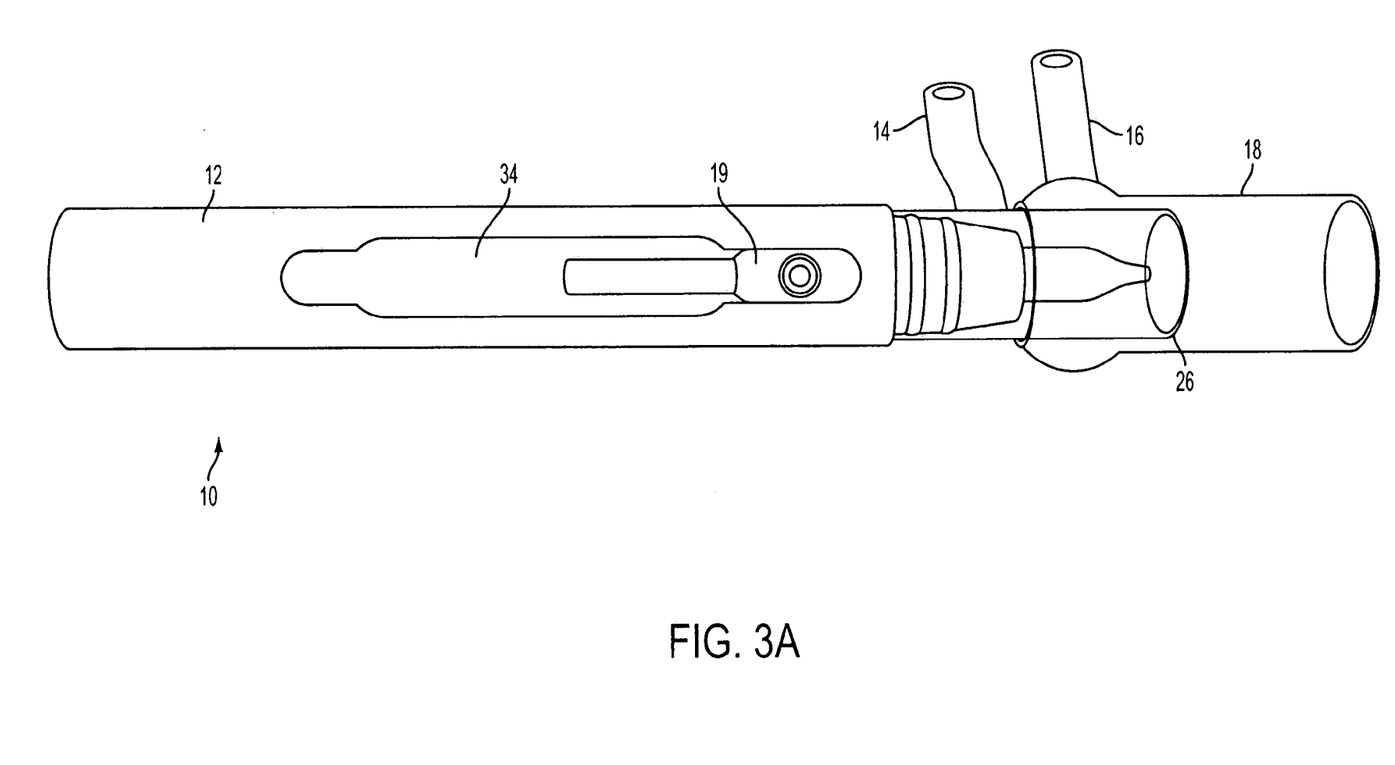
FIG. 3A is a diagram of the short torch with an attached adapter and HEN in accordance with an embodiment of the present invention.
Figure 3B:
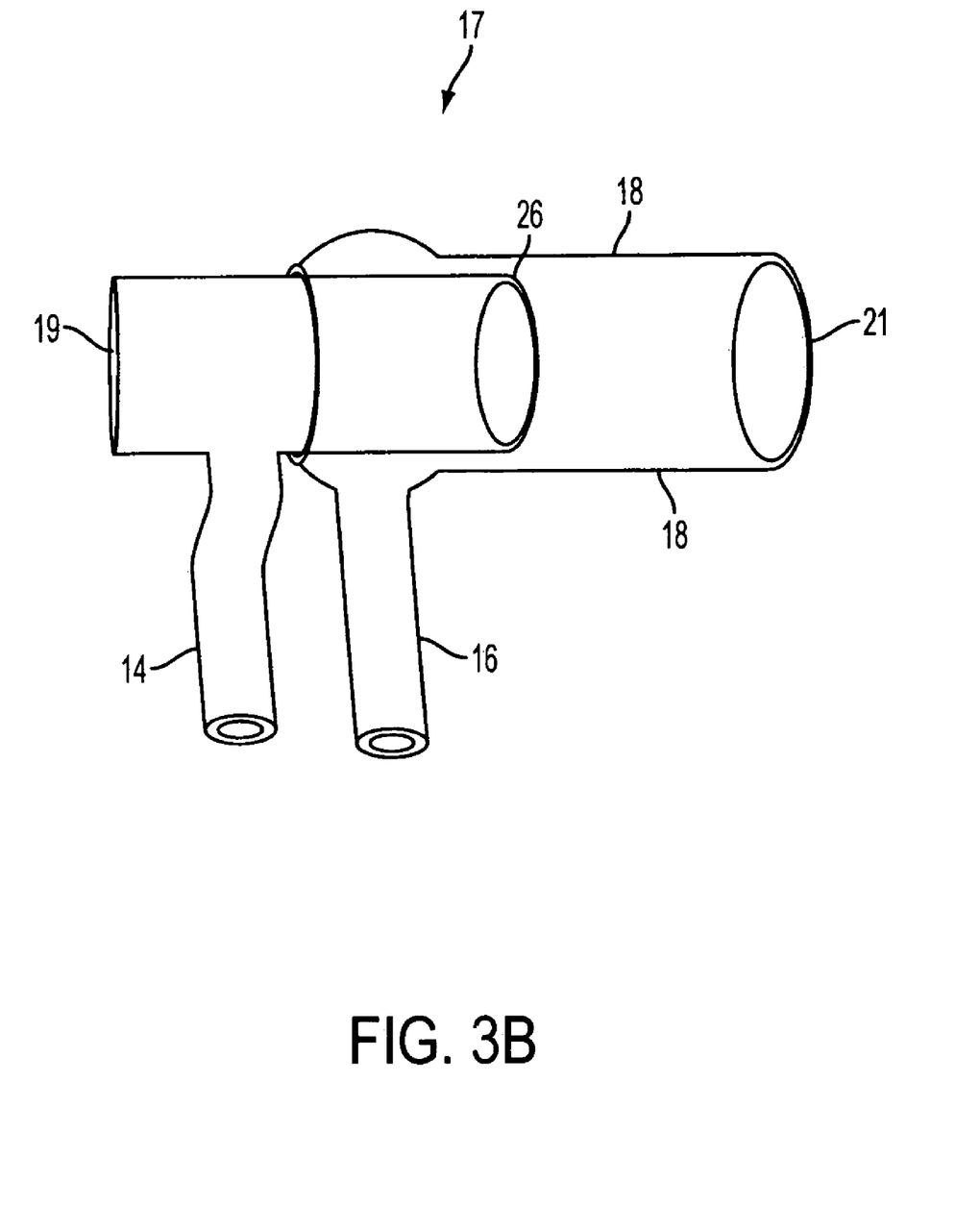
FIG. 3B is a diagram of a short torch in accordance with an embodiment of the present invention.

The torch 17 comprises an inner tube 26, an outer tube 18, an intermediate inlet gas tube 14, a gas inlet outer tube 16, an input 19, and an output 21 (see FIG. 3B). The material comprising the torch 17 is preferably borosilicate glass. Exemplary dimensions of the short torch design 10 will now be discussed. Since the dimensions of the short torch design 10 are adaptable to any type of conventional pneumatic nebulizer, the dimensions of the short torch design 10 may change depending on the size or type of nebulizer used. It should be appreciated by those skilled in the art that the following dimensions are exemplary and should not be used to limit the embodiment of the invention. The inner diameter 38 of the outer tube is 18 mm, the inner diameter 36 of the inner tube 26 is 14 mm. From the tip of the outer tube 18 to the tip of the inner tube 26 is 24 mm. From the tip of the outer tube 18 to the tip of the tapered open first end 30 of the adapter 12 is 38 mm. From the tip of the outer tube 18 to the neck 33 of the adapter 12 is 59 mm. From the tip of the outer tube 18 to the back of the solution connector 22 of the HEN 19 is 96 mm. From the tip of the outer tube 18 to the gas inlet outer tube is 32 mm. The inner diameter 44 of the gas inlet outer tube 16 and the inner diameter 40 of the intermediate inlet gas tube 14 are 6 mm. The distance between the gas inlet outer tube 16 and intermediate inlet gas tube 14 is 8 mm. The distance between the intermediate inlet gas tube 14 and the neck 33 of the adapter 12 is 7 mm.

The torch 17 is slidably mounted onto the tapered open first end 30 up to the neck 33 of the adapter 12. Teflon or other suitable material may be used to securely mount the torch 17 onto the adapter 12. A nebulizer such as HEN 19 is placed in the cavity 34 of the adapter 12 and slid forward toward the tip of the outer tube 18. An optimum distance between the tip of the nozzle of the HEN 19 and the tip of the outer tube is 2-5 mm. The adapter 12 securely maintains the HEN 19 in place to achieve the optimum distance between the tip of the outer tube and the nozzle of the HEN 19. That is, the short torch design 10 is structured and arranged such that the torch 17 is shortened compared to conventional torches and the adapter has a specific size and length of a cavity 34 to allow the HEN 19 to be a predetermined distance from the tip of the outer tube 18 of the torch 17.

Key dimensions of the HEN 19 with respect to other nebulizers are provided in Table 1 to show that the nebulizer tip dimensions (and resulting primary aerosol) will be similar under proper operating conditions.

The nebulizer gas is directed through the HEN 19 and is controlled by an external mass flow controller (not shown). A test solution is delivered to the HEN 19 using a syringe pump (not shown).

Analytical characteristics of the HEN 19 are determined preferably using an Elan 6000 ICPMS system manufactured by Perkin-Elmer/Sciex Corp., under the operating conditions listed in Table 2. All analytical data are obtained under standard laboratory conditions (e.g., not in a clean-room environment). The system is optimized daily for maximum signal ion intensity of $^{103}Rh^+$. All data are collected in the peak-hopping mode with a dwell time of 20 ms and total integration time of 1 s/mass unless otherwise noted. The lens voltage is auto-optimized for each m/z.

For analytical measurements, a 10 ng/mL, multielement stock solution is prepared by diluting 1000 µg/mL stock solutions such as manufactured by Inorganic Ventures with 2% high-purity $HNO_3$ such as Optima grade manufactured by Fisher Scientific in 18.3 MΩ·cm distilled deionized water (DDW).

Figure 4:
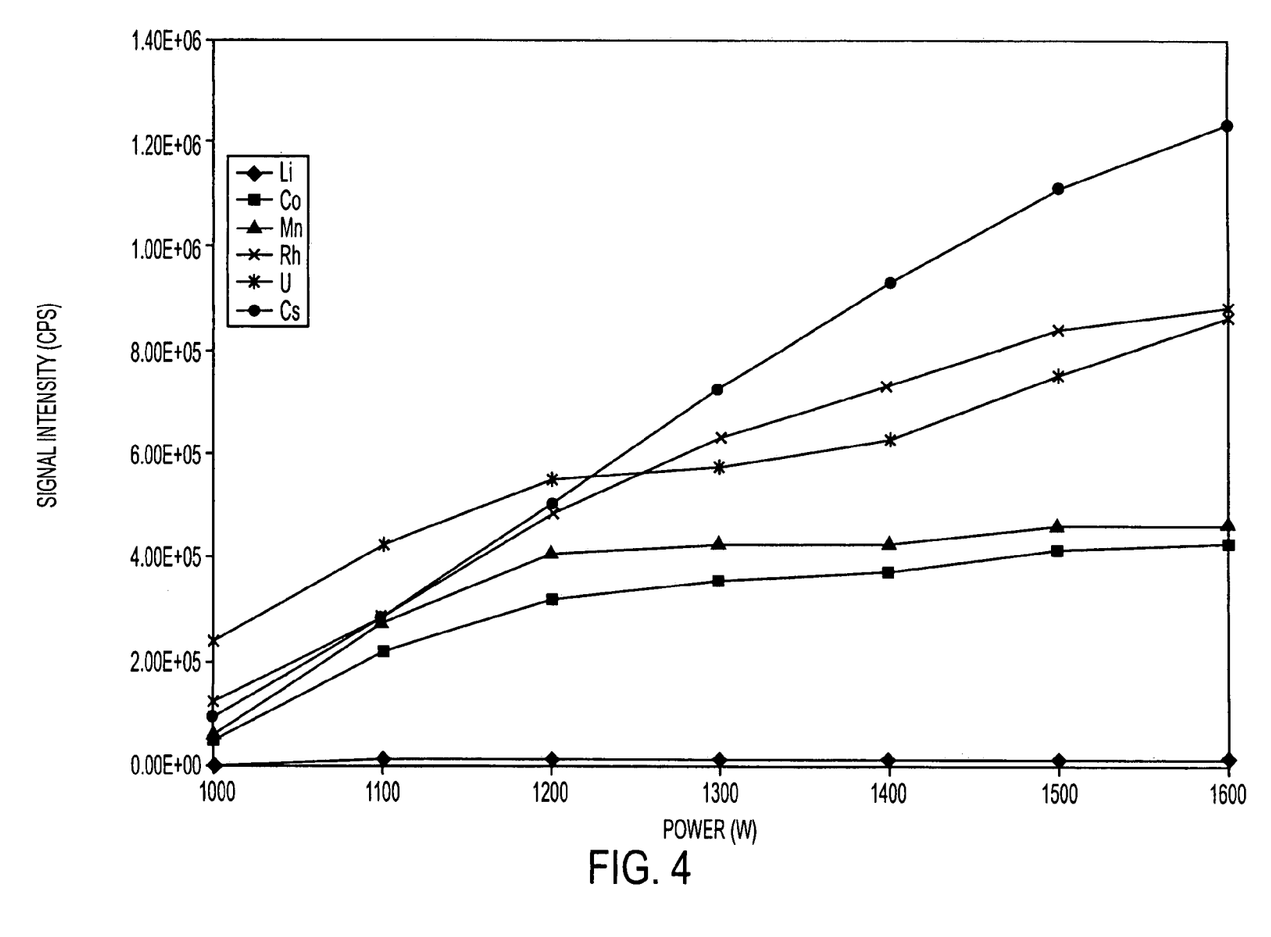
FIG. 4 is a graph illustrating signal intensity as a function of RF power, wherein a solution uptake rate, nebulizer gas flow rate, and intermediate gas flow rate are 85 µL/min, 0.26 L/min, and 1.5 L/min, respectively.
Figure 5:
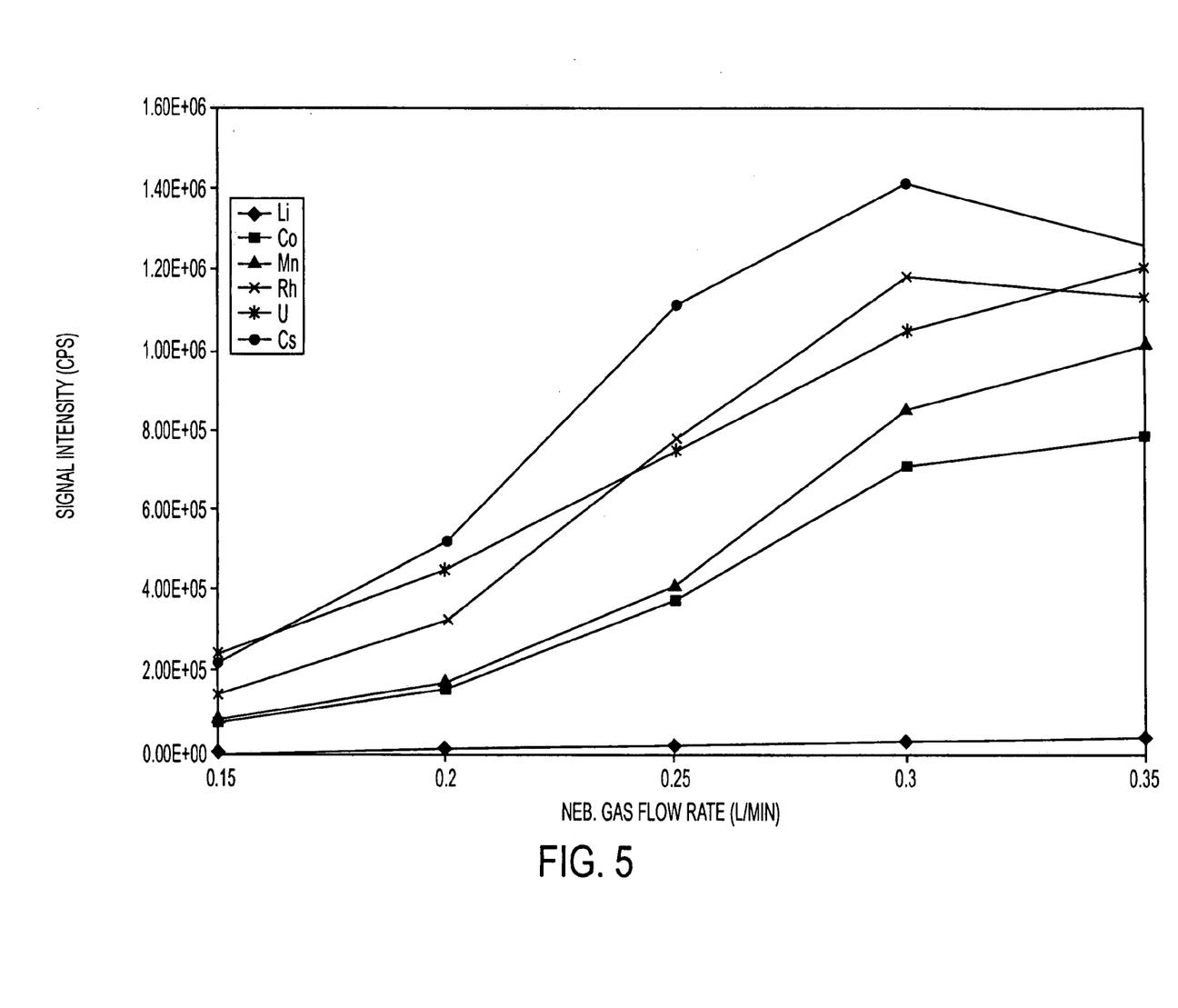
FIG. 5 is a graph illustrating signal intensity as a function of nebulizer gas flow rate, wherein the solution uptake rate, radio frequency (RF) power, and intermediate gas flow rate are 85 µL/min, 1500 W, and 1.5 L/min, respectively.
Figure 6:
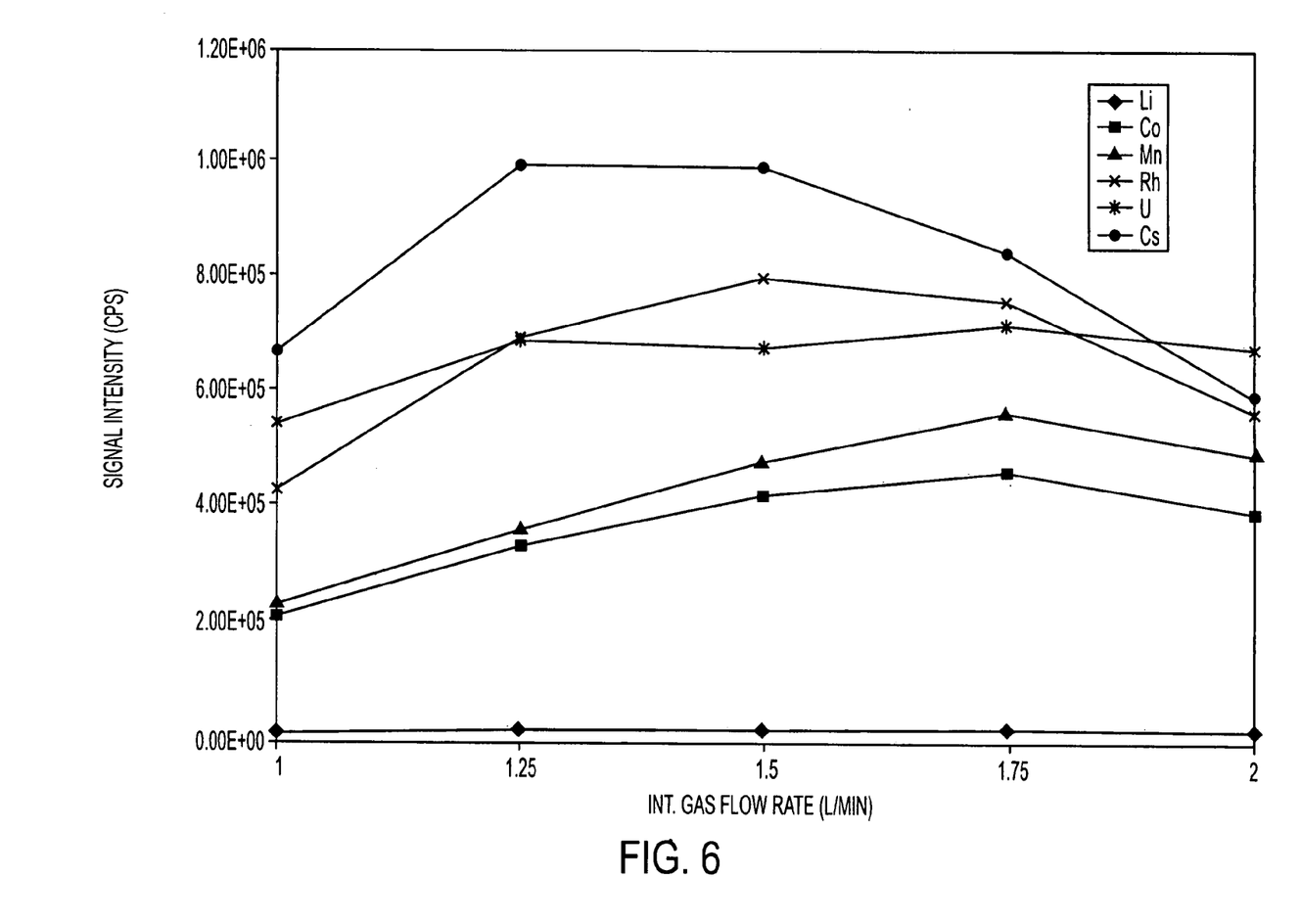
FIG. 6 is a graph illustrating signal intensity as a function of intermediate gas flow rate, wherein the solution uptake rate, RF power, and nebulizer gas flow rate are 85 µL/min, 1500 W, and 0.26 L/min, respectively.

Plots of signal intensity as a function of RF power, nebulizer gas flow rate, and intermediate gas flow rate are shown in FIGS. 4-6 for several elements across the mass range using the HEN 19 and for an optimum solution uptake rate of 85 µL/min. The short torch adapter design 10 when used with the HEN 19 optimizes under conditions similar to those used by a Direct Injection High Efficiency Nebulizer (DIHEN) and a demountable-Direct Injection High Efficiency Nebulizer (d-DIHEN). In particular, the short torch adapter optimizes at high powers (1500 W), low nebulizer gas flow rates (0.26 L/min), and at low solution uptake rates (85 µL/min). These conditions are not surprising, as the nebulizer tip dimensions of the HEN 19 are very similar to those of the DIHEN and d-DIHEN, therefore, the aerosol produced by each nebulizer should be similar. Since the position of each nebulizer with respect to the top of the intermediate tube of the torch is almost identical, the optimum operating conditions should therefore be the same.

Sensitivity, precision, and detection limits obtained with the short torch design 10 using the HEN 19 interface are presented in Table 3 for a solution uptake rate of 85 µL/min. The sensitivity obtained with the short torch design 10 using the HEN 19 is comparable to that obtained with the DIHEN, and slightly worse than the d-DIHEN. The precision, however, is improved at 85 µL/min compared to the DIHEN and d-DIHEN, and detection limits are similar for all three nebulizers. Table 4 shows the effect of a solution uptake rate on sensitivity and precision. Generally, as the solution uptake rate is decreased, sensitivity and precision are negatively affected. For the short torch design 10 using the HEN 19, this decrease in precision is not as severe compared to the DIHEN, and is similar to that obtained with the d-DIHEN. At solution flow rates below 20 µL/min, it was not possible to operate the short torch design 10 using the HEN 19 arrangement due to poor nebulization.

Oxide and doubly charged ratios obtained with the short torch design 10 using the HEN 19 arrangement compared to the DIHEN are shown in Table 5. In general, direct injection nebulizers typically suffer from worse oxide ratios than conventional nebulizer-spray chamber arrangements due to the introduction of 100% of the solution into the plasma. Compared to the DIHEN, the short torch design 10 using the HEN 19 arrangement has comparable oxide ratios, regardless of the solution uptake rate. This is somewhat surprising, as the nebulizer gas flow rate for the HEN 19 is much higher than for the DIHEN, which should increase the axial velocity of the aerosol, thereby reducing residence time within the plasma and increasing oxide ratios. One possible explanation for this observation is that the HEN 19 is positioned further back from the plasma than the DIHEN, which may help slow the aerosol down and increase its residence time within the plasma.

The short torch design 10 is provided as a modified sample introduction system to allow the use of conventional pneumatic nebulizers as direct liquid sample introduction systems. Similar analytical figures of merit are obtained using this new interface compared to other direct injection nebulizers such as the DIHEN and d-DIHEN. The short torch design 10 is advantageous in that it provides an inexpensive method of direct liquid sample introduction using the less expensive conventional pneumatic nebulizers. Additionally, due to its design, any conventional nebulizer may be used as a direct injection nebulizer.

That is, the short torch design 10 described in accordance with the embodiment of the present invention provide a means of achieving the analytical performance advantages of direct injection nebulizers while using the less expensive, more cost efficient conventional and micro-nebulizers. Due to the widespread use and availability of such devices, nearly all analytical laboratories can benefit from the advantages of direct sample introduction. Additionally, the short torch design 10 can accommodate nearly all commercially available conventional and micro-nebulizers, allowing the user to choose the optimal nebulizer type for the sample type to be analyzed. For example, aqueous samples could be analyzed using a HEN while biological samples with a high total dissolved solids content that would clog a HEN, such as urine or blood, could be analyzed using a concentric nebulizer with larger solution capillary dimensions. Alternatively, the PFA may be utilized for direct analysis of ultrapure semiconductor materials, especially when the test solution must not be in conduct with glassware to reduce changes of test solution contaminations. Such benefits multiply the analysis methods available to the user, providing even greater flexibility for elemental and isotopic ratio analysis.

In general, embodiments of the short torch design 10 described herein can offer several distinct advantages, listed below, over both direct injection nebulizers, and the nebulizer-spray chamber arrangement utilizing conventional or micro-nebulizers, such as: (1) Cost: 10 to 100 times lower in cost than other direct injection nebulizers, the DIHEN and DIN (approximately $250, depending on nebulizer, versus $2,000 and $20,000, respectively;) (2) Sample size: 10 to 3000 times less sample is consumed using the short torch design than when the same nebulizer is operated using a spray chamber; (3) Sample transport: 100% of the sample is delivered to the plasma compared to 1 to 20% when operated using a spray chamber; (4) Waste generation: No secondary waste is generated using the short torch design, while up to 3 mL/min is produced using a spray chamber; (5) Solution pump: Standard peristaltic, syringe pumps, or gas displacement mechanisms can be used to deliver solution to the nebulizer with the short torch design; no need for high-pressure pumps similar to those used for the DIN; (6) Precision: Improved over operation with a spray chamber, especially at lower solution uptake rates; (7) Sensitivity: Improved over operation with a spray chamber, especially at lower solution uptake rates; and (8) Memory Effects: Reduced in comparison with a spray chamber.

Other important advantages using the embodiments of the short torch design 10 described herein are realized in speciation analysis, such as microscale high performance liquid chromatography (µHPLC) and capillary electrophoresis (CE) using the elemental and isotopic selectivity of ICPMS. In these and other speciation techniques, the flow rate of the separation technique must be matched with the optimal flow rate of the interface to the ICPMS. Additionally, the efficiency of the separation is also affected by the dead volume of the system. Interfacing such microscale separation techniques with a spray chamber can lead to post-column band broadening, thereby reducing the achievable resolution. The short torch-adapter interface embodiments described herein provide a means of using low sample consumption nebulizers as an alternative to the more expensive direct injection nebulizers while maintaining the advantages of flow rate compatibility and minimal band broadening.

In the age of "green" chemistry, the short torch-adapter embodiments described herein provide a means to reduce the amount of chemical wastes generated during analysis. With 100% of the sample being transported to the plasma and improved performance of the nebulizer at lower solution uptake rates, the described design can reduce both sample and solvent consumption. This is particularly important when either expensive or environmentally unfriendly solvents have to be used.

While the invention has been shown and described with reference to certain embodiments thereof, it should be understood by those skilled in the art that various changes in form and details may be made therein without departing from the spirit and scope of the invention as defined by the appended claims and equivalents thereof.

TABLE 1

Critical Dimensions and Parameters for the HEN in Comparison to the DIHEN, LB-DIHEN, and Conventional TR-30 nebulizers.

| | HEN[b] (HEN-170-AA) | DIHEN (DIHEN-170-AA) | d-DIHEN (DIHEN-30-AA) | Conventional Nebulizer[b] (TR-30-AA) |
|---|---|---|---|---|
| Solution capillary i.d. (μm) | 70-110 | 104 | 100 | 220-320 |
| Capillary wall thickness (μm) | 15-40 | 20 | 21 | 15-40 |
| Solution capillary o.d. (μm) | 100-190 | 144 | 142 | 250-400 |
| Gas orifice i.d. (μm) | 150-200 | 173 | 175 | 350-450 |
| Capillary annulus area (mm$^2$) | 0.0038-0.0095 | 0.0085 | 0.00785 | 0.05-0.10 |
| Gas annulus area (mm$^2$) | 0.007-0.01 | 0.0094 | 0.00822 | 0.03-0.04 |

TABLE 2

Instrumental Operating Conditions for the Ar ICPMS.

| | |
|---|---|
| ICPMS System | PE-Sciex Elan 6000 |
| RF power, W | 1500, 1000-1600 |
| Nominal frequency, MHz | 40 |
| RF generator type | Free-running |
| Induction coil circuitry | 3-turn coil, PLASMALOK ™ |
| Sampling depth (above load coil), mm | 11 |
| Sampler (orifice diameter, mm) | Platinum, 1.1 |
| Skimmer (orifice diameter, mm) | Platinum, 0.9 |
| Outer gas flow rate, L/min | 20 |
| Intermediate gas flow rate, L/min | 1.5, 0.8-1.6 |
| Sample introduction system | |
| Solution flow rate, μL/min | 20-85 |
| Nebulizer gas flow rate, L/min | 0.26, 0.15-0.35 |
| Capillary position below intermediate tube, mm | 4 |
| Data acquisition parameters | |
| Scan mode | Peak hopping |
| Points/mass | 1 |
| Resolution, amu | 0.7 |
| Sweeps/Reading | 10 |
| Readings/Replicate | 5 |
| Replicates | 11 |
| Dwell time/mass, ms | 20 |
| Integration time, ms | 1000 |
| Replicates | 11 |

TABLE 4

Relative Sensitivities (MHz/ppm) and Precision (% RSD) Obtained for the HEN, DIHEN, and d-DIHEN at Low Solution Uptake Rates[a] and 1500 W.

| | Solution Uptake Rate | | | | | | |
|---|---|---|---|---|---|---|---|
| | 20 μL/min | | 40 μL/min | | | | |
| Isotope | HEN | | HEN | | DIHEN | | d-DIHEN |
| $^7$Li | 0.5 | (2.7) | 1.6 | (2.6) | 3 | (2.5) | 7.4 (2.2) |
| $^{51}$V | 8 | (1.6) | 21 | (1.2) | 20 | (1.7) | 48 (2.2) |
| $^{55}$Mn | 8 | (1.4) | 24 | (1.6) | 25 | (1.2) | 63 (2.2) |
| $^{59}$Co | 7 | (1.5) | 21 | (1.7) | 18 | (1.2) | 56 (1.9) |
| $^{60}$Ni | 2 | (2.3) | 4.8 | (1.4) | — | — | 11 (2.2) |
| $^{63}$Cu | 4 | (1.9) | 12 | (1.4) | — | — | 35 (1.8) |
| $^{75}$As | 3 | (1.8) | 11 | (1.1) | 4 | (1.3) | 25 (1.7) |
| $^{82}$Se | 0.3 | (3.2) | 1.1 | (2.3) | 0.4 | (3.1) | 2.5 (1.8) |
| $^{88}$Sr | 13 | (2.0) | 39 | (1.4) | 68 | (1.8) | 82 (2.3) |
| $^{103}$Rh | 13 | (1.7) | 43 | (1.5) | 50 | (1.6) | 93 (1.6) |
| $^{115}$In | 16 | (1.1) | 51 | (2.4) | — | — | 106 (1.8) |
| $^{133}$Cs | 22 | (1.7) | 64 | (1.3) | 86 | (1.4) | 113 (1.8) |
| $^{208}$Pb | 11 | (1.4) | 27 | (1.6) | 37 | (0.9) | 51 (1.6) |
| $^{232}$Th | 5 | (2.5) | 24 | (1.1) | — | — | 91 (1.7) |
| $^{238}$U | 17 | (1.4) | 44 | (0.8) | 80 | (0.9) | 93 (1.6) |

[a]The nebulizer gas flow rate is 0.26, 0.16, and 0.25 L/min for the HEN, DIHEN, and d-DIHEN, respectively.

TABLE 3

Typical Sensitivity, Relative Detection Limits, and Precision in ICPMS Obtained with the HEN, DIHEN, and d-DIHEN Nebulizers.[a]

| | Sensitivity (MHz/ppm) | | | Detection Limit (ng/L) | | | Precision (% RSD)[b] | | |
|---|---|---|---|---|---|---|---|---|---|
| Isotope | HEN | DIHEN | d-DIHEN | HEN | DIHEN | d-DIHEN | HEN | DIHEN | d-DIHEN |
| $^7$Li | 6 | 8.2 | 9.3 | 5 | 2 | 2 | 1.2 | 0.6 | 1.4 |
| $^{24}$Mg | 34 | 20 | 26 | 48 | 7 | 47 | 0.9 | 0.6 | 1.5 |
| $^{51}$V | 96 | 30 | 88 | 5 | 2 | 6 | 0.4 | 0.8 | 0.6 |
| $^{55}$Mn | 120 | 65 | 113 | 1 | 2 | 10 | 0.5 | 0.7 | 0.7 |
| $^{59}$Co | 98 | 56 | 110 | 0.4 | 0.9 | 2 | 0.4 | 0.8 | 0.9 |
| $^{60}$Ni | 22 | 9.9 | 25 | 4 | 12 | 8 | 0.4 | 0.7 | 0.6 |
| $^{63}$Cu | 51 | 25 | 41 | 12 | 10 | 33 | 0.2 | 0.6 | 1.0 |
| $^{75}$As | 44 | 4.5 | 36 | 3 | 17 | 1 | 0.4 | 1.3 | 0.9 |
| $^{82}$Se | 4.2 | 0.6 | 3.4 | 9 | 47 | 12 | 0.6 | 1.4 | 1.3 |
| $^{88}$Sr | 146 | 95 | 161 | 12 | 0.9 | 1 | 0.3 | 0.8 | 0.6 |
| $^{103}$Rh | 143 | 91 | 167 | 0.6 | 0.6 | 0.3 | 0.4 | 0.9 | 0.5 |
| $^{115}$In | 158 | 113 | 193 | 1 | 0.6 | 0.5 | 0.4 | 0.6 | 0.6 |
| $^{133}$Cs | 158 | 130 | 201 | 0.8 | 0.6 | 0.4 | 0.4 | 0.9 | 0.6 |
| $^{208}$Pb | 63 | 76 | 115 | 10 | 2 | 3 | 0.5 | 0.5 | 0.4 |
| $^{232}$Th | 77 | 66 | 167 | 3 | 0.6 | 0.5 | 2.0 | 1.2 | 0.5 |
| $^{238}$U | 128 | 99 | 175 | 0.5 | 0.3 | 0.4 | 0.6 | 0.8 | 0.4 |

[a]The nebulizer gas flow rate is 0.26 L/min for the HEN, 0.25 L/min for the DIHEN and 0.25 L/min for the d-DIHEN. The solution uptake rate is 85, 85, and 110 μL.
[b]Measured over 6 minutes using a 10 μg/L multielement solution, N = 11.

TABLE 5

Oxide and Doubly Charged (%) Ratios with the HEN and DIHEN
Measured at Different Solution Uptake Rates and 1500 W.[a]

| | Solution Uptake Rate | | | | | | | |
|---|---|---|---|---|---|---|---|---|
| | 5 μL/min | 10 μL/min | 20 μL/min | 40 μL/min | | 85 μL/min | | |
| | DIHEN | DIHEN | HEN | HEN | DIHEN | HEN | DIHEN | DIHEN[b] |
| $BaO^+:Ba^+$ | 0.02% | 0.02% | 0.06% | 0.70% | 0.11% | 2.0% | 0.29% | 0.55% |
| $CeO^+:Ce^+$ | 0.50% | 0.78% | 1.9% | 2.3% | 2.8% | 3.3% | 7.6% | 27% |
| $YO^+:Y^+$ | 0.22% | 0.29% | 0.70% | 0.90% | 0.98% | 1.3% | 2.4% | 6.6% |
| $TbO^+:Tb^+$ | 0.21% | 0.33% | 0.77% | 1.0% | 1.3% | 1.8% | 3.2% | 8.1% |
| $HoO^+:Ho^+$ | 0.12% | 0.17% | 0.26% | 0.40% | 0.61% | 0.8% | 1.4% | 2.2% |
| $ThO^+:Th^+$ | 0.88% | 1.4% | 3.1% | 3.9% | 4.7% | 6.0% | 14% | 43% |
| $UO^+:U^+$ | 0.83% | 1.3% | 2.9% | 3.8% | 4.0% | 5.0% | 9.4% | 23% |
| $Ba^{2+}:Ba^+$ | 1.2% | 1.4% | 2.1% | 2.3% | 2.1% | 4.4% | 1.9% | 1.1% |

[a]The nebulizer gas flow rate is 0.26 and 0.18 L/min for the HEN and DIHEN, respectively, unless otherwise indicated.
[b]Nebulizer gas flow rate = 0.25 L/min

What is claimed is:

1. A torch apparatus for providing direct liquid sample introduction using a nebulizer, comprising:
   a short torch having an inner tube and an outer tube; and
   an elongated adapter having a cavity for receiving the nebulizer and positioning a nozzle tip of the nebulizer a predetermined distance from a tip of the outer tube of the short torch.

2. The torch apparatus of claim 1, wherein said predetermined distance comprises about 2-5 mm.

3. The torch apparatus of claim 1, wherein said elongated adapter comprises a high temperature resistant material.

4. The torch apparatus of claim 3, wherein said high temperature resistant material comprises Delrin.

5. The torch apparatus of claim 1, wherein said short torch comprises borosilicate glass.

6. The torch apparatus of claim 1, wherein said nebulizer comprises a High Efficiency Nebulizer (HEN).

7. The torch apparatus of claim 1, wherein the nebulizer comprises a pneumatic nebulizer.

8. The torch apparatus of claim 1, wherein the adapter has a closed end and an open end.

9. The torch apparatus of claim 8, wherein said open end of said adapter is tapered.

10. The torch apparatus of claim 7, wherein said open end of said adapter begins at a neck of said adapter.

11. The torch apparatus of claim 1, wherein said torch short torch is shorter than a conventional torch.

12. A method of providing direct liquid sample introduction using a nebulizer, comprising:
    providing a short torch having an inner tube and an outer tube; and
    receiving the nebulizer via an elongated adapter having a cavity and positioning a nozzle tip of the nebulizer a predetermined distance from a tip of the outer tube of the short torch.

13. The method of claim 1, wherein said predetermined distance comprises 2-5 mm.

14. The method of claim 1, wherein said elongated adapter comprises a high temperature resistant material.

15. The method of claim 13, wherein said high temperature resistant material comprises Delrin.

16. The method of claim 11, wherein said short torch comprises borosilicate glass.

17. The method of claim 11, wherein said nebulizer comprises a High Efficiency Nebulizer (HEN).

18. The method of claim 11, wherein said nebulizer comprises a pneumatic nebulizer.

19. The method of claim 11 further comprising:
    providing a closed end and an open end for said adapter.

20. The method of claim 18 further comprising:
    tapering said open end of said adapter.

* * * * *